United States Patent [19]

Masuda

[11] 4,077,610

[45] Mar. 7, 1978

[54] METHOD AND APPARATUS FOR PASSING AN ARTICLE THROUGH AN INTERIOR OF A PIPE

[76] Inventor: Senichi Masuda, 40-10-605, 1-chome, Hishigahara, Kita, Tokyo, Japan

[21] Appl. No.: 752,406

[22] Filed: Dec. 20, 1976

Related U.S. Application Data

[63] Continuation of Ser. No. 646,950, Jan. 6, 1976, abandoned.

[51] Int. Cl.² .......................................... A61M 25/00
[52] U.S. Cl. .................................. 254/134.4; 128/348
[58] Field of Search ................... 254/134.4, 134.3 FT; 128/2 M, DIG. 9, 348, 349

[56] References Cited

U.S. PATENT DOCUMENTS

| | | | |
|---|---|---|---|
| 3,006,607 | 10/1961 | Hamrick | 254/134.4 |
| 3,168,092 | 2/1965 | Silverman | 128/2 M |
| 3,433,214 | 3/1969 | Silverman | 128/2 M |
| 3,757,788 | 9/1973 | Renfroe | 128/2 M |
| 3,894,540 | 7/1975 | Bonner | 128/348 |

FOREIGN PATENT DOCUMENTS

| | | | |
|---|---|---|---|
| 4,972,372 | 7/1974 | Japan | 254/134.4 |
| 1,025,011 | 4/1966 | United Kingdom | 254/134.4 |
| 1,069,623 | 5/1967 | United Kingdom | 254/134.4 |

Primary Examiner—Robert C. Watson
Attorney, Agent, or Firm—Price, Heneveld, Huizenga & Cooper

[57] ABSTRACT

A turned-over or inverted section is formed at one end of a flexible, fluid impervious tube by turning the tube inside out and folding it back up on itself. With the turned-over end inserted in a pipe or conduit, the folded over end is secured to the pipe and then a fluid differential is created between the inside of the tube in the pipe and the inside of the pipe ahead of the tube which differential is great enough to cause the turned-over end of the tube to migrate along the pipe from one end to the other by drawing the tube into the pipe from the end which is not attached to the pipe. In this manner, a flexible tube can be installed in a pipe irrespective of the complex configuration into which the pipe is bent or the variations in cross-sectional shape which may exist along the length of the pipe. The disclosure also includes an apparatus providing a pipe engaging means for forming the inverted end of the tube and sealing it to the end of the pipe. The apparatus also included a chamber for pressurized fluid in which a quantity of the collapsed tube is stored in a manner to be progressively released as the tube is inserted in the pipe.

9 Claims, 8 Drawing Figures

METHOD AND APPARATUS FOR PASSING AN ARTICLE THROUGH AN INTERIOR OF A PIPE

This is a continuation of application Ser. No. 646,950 filed Jan. 6, 1976, now abandoned.

CROSS REFERENCE TO RELATED APPLICATION

The present invention relates to a method and apparatus for passing a tube made of rubber, plastics or other suitable material through an interior of a pipe, especially through an interior of a pipe bent in a complexed shape, from its one end to the other end.

Heretofore, in order to pass a line or lines such as a cable or the like through an interior of a pipe from one end to the other end, the method most frequently used has been one in which a metallic wire having rigidity as well as flexibility such as a piano wire, a steel wire, etc. is fed into one end of the pipe until the wire reaches the other end. However, according to this method, when the pipe through which the wire is to be passed is bent, feeding of the metallic wire becomes very difficult and normally, passing the wire through the pipe takes a lot of time or even becomes impossible. Especially, in case of pipes bent in a complicated manner, it was definitely impossible to pass a metallic wire through the pipe.

It is one object of the present invention to overcome the aforementioned difficulties and to provide means for passing an article through an interior of a pipe freely, quickly, cheaply and reliably, no matter how complicated the cross-sectional shape of the pipe and no matter how complex the bent shape of the pipe.

According to one feature of the present invention, there is provided a method for passing an article through an interior of a pipe, characterized by the steps of fixing one end of a freely bendable and pressure-proof of tight tube to or prominate one end of a pipe through which an article is to be passed in such manner that air-tightness may be maintained about its entire circumference; inserting said tube into the interior of said pipe at said one end in such manner as to form in the interior of said pipe a turned-over section where the inside of said tube is folded to the outside, that is, inverted and establishing a pressure difference between the opposite sides of said turned-over section so that pressure directed into the side of inserted tube towards the other end of the pipe can be exerted upon said turned-over section; whereby said turned-over section may be advanced along the inner surface of said pipe, while folding said tube from the inside to the outside, until the turned-over section reaches the other end of said pipe, and thus said tube can be passed through the interior of said pipe.

According to the aforementioned method, no matter how compressed the cross section of the pipe and no matter how complicated the bends in the pipe, the passage of an article through the interior of the pipe can be achieved easily, quickly, reliably and extremely cheaply. The invention is also effective in the same manner to pass a line or lines such as cables through the pipe, or to convey an object such as a measuring instrument or a fiberscope to a predetermined position within the pipe.

The other end of the pipe could be connected to a vacuum pump to establish a negative pressure in the space in front of said turned-over section as one method of generating the above-described pressure difference at the turned-over section. The space behind said turned-over section could be made to have a positive pressure with respect to the space in front of said turned-over section by attaching one end of said tube to a pressurized chamber consisting, for example, of an air-tight casing, one end of said tube being fixed in an air-tight manner about its entire circumference to an annular fixture having an opening provided in a wall of said pressurized chamber. The annular fixture is then coupled to one end of the pipe and said tube is pushed into the interior of the pipe through said opening while being turned over or inside-out by pressure feeding an appropriate fluid such as air, water, oil, etc. into said pressurized chamber by means of a pump, whereby said turned-over section may be formed within the pipe and also may be advanced by said pressure.

In addition, while the other end of the tube could be tied up in order to maintain said air-tightness, if the tube itself collapases due to said pressure difference, then there is no need to tie up the other end of the tube, instead, on the inlet side of the pipe the tube, for example, is first wound on a take-up reel within said pressurized chamber and as the turned-over section is advanced, the tube could be paid off from the reel to be fed into the pipe.

Also, by preliminarily contracting a tube to shape it cross-sectionally into a tape-like, star-like, zigzag, H-like shape or any other arbitrary cross-sectional configuration, handling and feeding of the tube is facilitated, and such tubes could be used after first storing them within a case (cassette) provided with a take-up reel. Alternatively, the tube could be folded in its lengthwise direction to compress in length by preliminarily forming folded creases in a diaphragm-like, bellows-like, paper-lantern-like, or any other shape around its outer circumference over its entire length. Such form of use is convenient in the case where a sensing head such as a measuring instrument or a fiberscope is inserted at any desired position within the pipe and it is moved while continuing observation.

The method for passing an article through an interior of a pipe according to the present invention can be also practiced as an apparatus for passing a line or lines through an interior of a pipe in which after a tube has been once passed through the pipe, a desired linear object such as a cable is tied to the tube and then passed through the pipe. Alternatively, the purpose of passing a line through a pipe can be realized by tying the desired linear object such as a cable to the other end of the tube and passing it jointly with the tube from one end of the pipe to the other end. In addition, not only for the purpose of passing a line such as a cable, but also the method and apparatus according to the present invention can be utilized for the purpose of feeding or passing any desired object such as the sensing head of a measuring instrument or fiberscope or a gamma ray source through the interior of a pipe.

Now the novel method and apparatus for passing an article through an interior of a pipe according to the present invention will be described in more detail with respect to their operating principle and features in connection to the preferred embodiments illustrated in the drawings, in which:

DETAILED DESCRIPTION OF THE PREFERRED EMBODIMENTS

Figure 1:
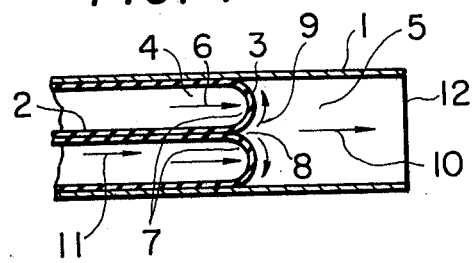
FIG. 1 is a cross section view showing the principle of advance of a tube turned-over section within a pipe which forms an essence of the present invention.
Figure 2:
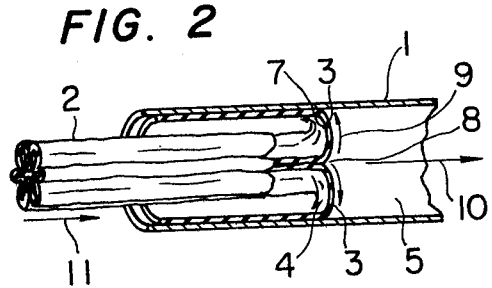
FIG. 2 is a perspective view of the same.
Figure 3:
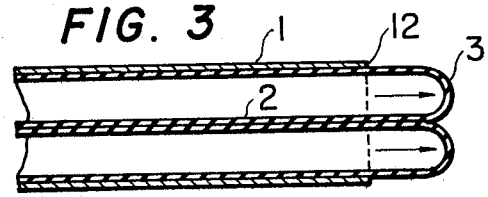
FIG. 3 is a schematic view showing a principle of the present invention.

Referring now to FIGS. 1 to 3 of the drawings, in an interior of a pipe 1, a tube 2 which has first been contracted has its inside folded to outside to form an inverted or turned-over section 3. Between the space 4 behind the end of the said turned-over section 3 and the space 5 in front of the end of said turned-over section 3 a pressure differential is applied so that a pressure, directed from the former to the latter as represented by an arrow 6 is exerted upon the back face of said turned-over section 3. As a result, said turned-over section 3 advances in the direction of an arrow 10 along the inner surface of the pipe 1 while the inside surface 8 is being folded or rolled in the direction of an arrow 9, advancing in the manner of a flexible track vehicle. Simultaneously, the tube 2 is drawn from left to right in the direction of an arrow 11, until said turned-over section 3 appears outside of the other end 12 of the pipe as shown in FIG. 3, when the passing of the tube 2 through the pipe 1 has been completed.

Figure 4:
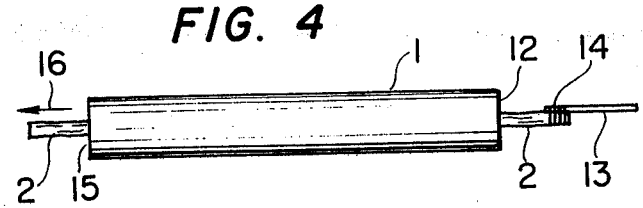
FIGS. 4 and 5 are schematic views showing a method of passing a line through a pipe according to the present invention.
Figure 5:
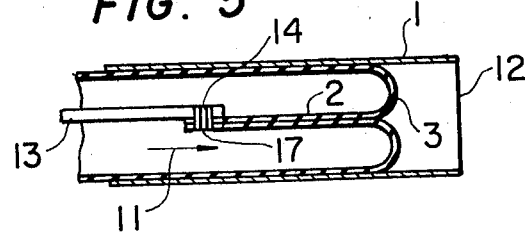

Subsequently, in order to pass a line, for example, through the pipe 1, after the tube 2 has been passed through a tube in the manner previously described, a cable 13 is tied to said tube 2 as by means of a wire 14 or the like at the outside of the outlet end 12 of the pipe as shown in FIG. 4 and said tube 2 is drawn in the direction of an arrow 16 at the inlet end 15 of the pipe 15 to pass said cable 13 through the interior of said pipe 1. Alternatively, as shown in FIG. 5, a cable 13 or the like is first tied to one end 17 of the tube 2 as by means of a wire 14, so that the cable 13 can be drawn into the pipe in the direction of an arrow 11 until it is drawn out of an outlet end 12 of the pipe 1 as said turned-over section 3 advances, and thereby the cable 13 is passed through the pipe.

Figure 6:
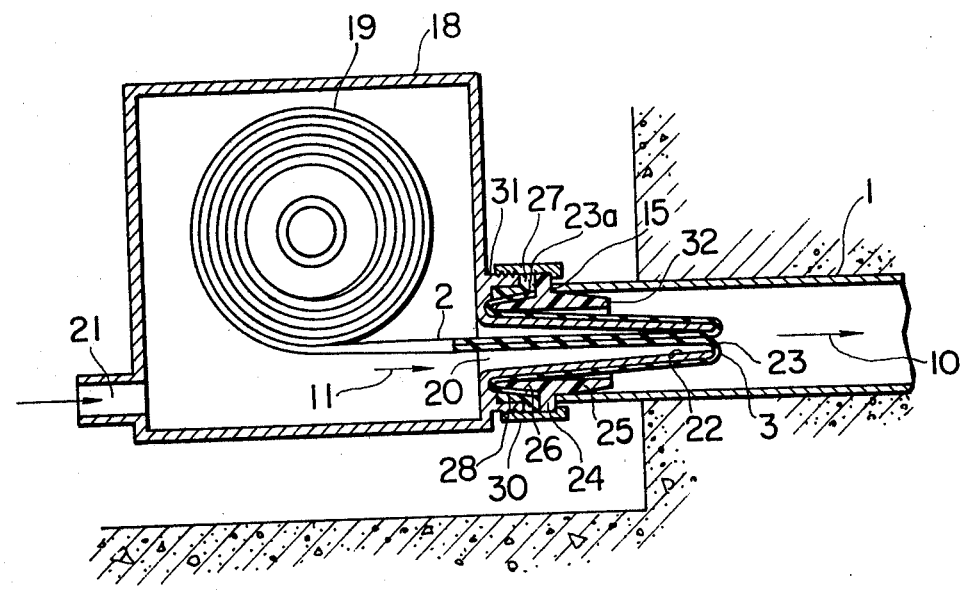
FIG. 6 is a longitudinal cross section view of one preferred embodiment of the present invention.
Figure 7:
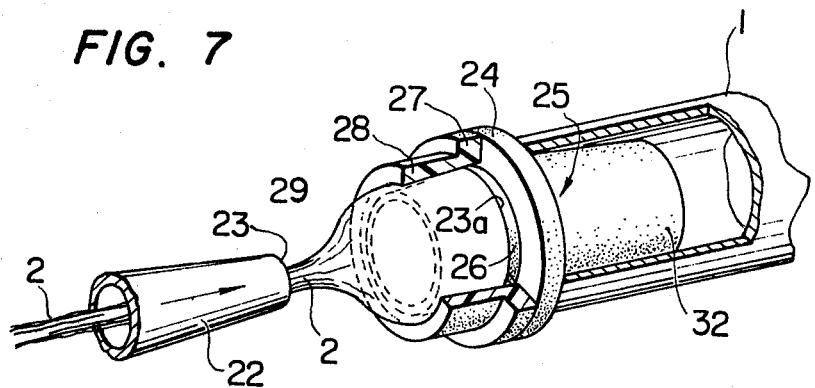
FIG. 7 is a partially exploded, perspective view of an essential part of the apparatus in FIG. 6.

FIG. 6 is a longitudinal, cross section view showing one preferred embodiment of the present invention, and FIG. 7 is a partially exploded, perspective view showing the tube fixture which forms an essential part of the apparatus in FIG. 6. In these figures, reference numeral 1 designates a pipe through which an article is to be passed and reference numeral 15 designates an inlet end of the pipe. Reference numeral 18 designates a pressurized chamber consisting of a casing, which forms a pressure differential generator that is essential for the subject invention, and which comprises an air-tight door, not shown, a reel 19 having a tube wound therearound and accommodated within the casing, an opening 20 for feeding a tube, a high pressure fluid inlet port 21 connected to a high pressure fluid source such as a pump, a compressor or a bomb, and a nozzle-like tube guide cylinder 22 projecting outwardly from said opening 20. To operate, said reel 19 is first loaded within said pressurized chamber 18 by opening said air-tight door and one end of said tube 2 is then drawn out through said opening 20 and said guide cylinder 22 to the outside of the outlet 23. The end 23a of the tube 2 is fitted or folded back over the bill-shaped guide cylinder 22 and then about the periphery of the inner end of a sleeve 25 of the mounting guide and clamping cylinder 26. The cylinder 26 is provided with a radially extending flange 24 made of rubber or plastic. A packing member 28 having a flange 27 made of rubber is fitted around the inner end 23a of the outer periphery of said guide cylinder 26 as shown in FIGS. 6 and 7. Subsequently, after the outlet 23 of said guide cylinder 22 has been inserted into the opening 29 of said guide cylinder 26 and fitted therein as shown in these figures, the flanges 24 and 27 are fixed to a mounting seat member 31 at the base portion of said guide cylinder 22 by means of an attachment or a fixing ring 30. In this manner, the tube 2 is fixed at its one end to the base portion of said guide cylinder 22 in an air-tight manner about its entire circumference. At the same time, said tube forms a turned-over section 3 at the tip end 23 of the guide cylinder 22. Thereafter, said guide cylinder is inserted into the inlet 15 of the pipe 1 with the flange 24 urged against the inlet end 15 to maintain air-tightness, the air-tight door of the pressurized chamber is closed and a pressurized fluid is introduced into the pressurized chamber through the inlet port 21. Thus, the pressure is at once applied to the space behind said turned-over section 3, so that said turned-over section advances in the direction of an arrow 10 as explained with reference to FIGS. 1 and 2, while the tube is being peeled off the reel 19 and fed in the direction of an arrow 11 to be passed through the pipe 1.

In FIGS. 6 and 7, reference numeral 32 designates another guide cylinder or outward extension of the sleeve 25 projecting oppositely to the guide cylinder or inward extension 26. The guide cylinder 32 serves to guide the sleeve 25 for concentric insertion into the pipe inlet 15. The above-referred to air-tight door is opened and closed upon loading and unloading of the reel 19 and during the operation of drawing out one end of the tube 2.

Figure 8:
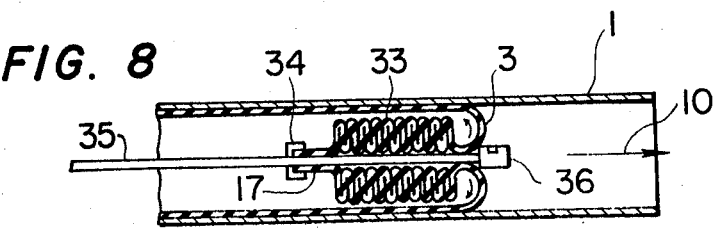
FIG. 8 is a longitudinal cross section view of an essential part of another preferred embodiment of the present invention.

FIG. 8 is a longitudinal cross-sectional view of a part in the proximity of the turned-over section 3 illustrating another preferred embodiment of the present invention. In this preferred embodiment, a tube which has first been compressed in its lengthwise direction as folded in a form similar to a paper lantern is employed, and the folded section 33 is adapted to advance in the direction of an arrow 10 jointly with the turned-over section 3 and is thus passed through the pipe. In this illustrated embodiment, a fiberscope 35 is fixed at one end 17 of the tube by means of a fixture 34, a head portion 36 of the fiberscope 35 projecting forwardly of said folded section 33, and thereby any portion within the pipe can be observed by the fiberscope 35. If a gamma ray source such as, for example, cobalt-60 is mounted at the head 36, then, of course, it is possible to achieve defect hunting of said pipe by means of an X-ray photograph or else by mounting a suitable brush and a liquid chemicals injector in place of the head 36 it is also possible to carry out internal washing of the pipe.

As described above, the present invention provides methods and means for freely passing an article through an interior of a pipe of every kind and every shape, so that the application of the invention extends over every operation which can be conducted by utilizing the operation of passing an article through a pipe and, therefore, the application is not limited to passing a line, feeding an article and internal washing only.

The embodiments of the invention in which an exclusive property or privilege is claimed are defined as follows.

1. The method of inserting a probe into a tube-like opening characterized by the steps of providing an elongated, flexible, fluid impervious, tubular element, folding said element to form an inverted end and inserting the inverted end into the opening, creating a pressure differential across the inverted end of the element such that a sufficiently higher pressure is exerted on said inverted end from the inside of said element to cause said inverted end to travel into the opening pulling said element from its other end into and through said opening, providing an instrument on the exterior of said element at said inverted end and pushing said instrument ahead by the unfolding action of said element as the element expands forwardly.

2. The method of inserting a probe as described in claim 1 wherein an elongated means is secured to said instrument, passing said means in sealing relationship through the wall of the tubular element.

3. The method of claim 1 wherein said tubular member is folded and compressed into a compact mass of bellows-like configurations capable of lengthwise, progressive unfolding as said mass travels through said opening.

4. The method of claim 1 wherein an elongated member attached to the instrument extends through the mass and is pulled with the instrument as the mass travels and unfolds.

5. An apparatus for passing an elongated, flexible, fluid impervious, tubular element through a tube-like member, said apparatus comprising: a chamber having a collar; an elongated, rigid, tubular nozzle projecting through said collar; one end of said tubular element being seated over the outside of said nozzle and folded back over the end thereof, said tubular element extending rearwardly through the center thereof; an annular sleeve surrounding said nozzle adjacent its base, said end of said tubular element being reversely bent over the end of said sleeve adjacent said base, means pressing said sleeve toward said collar for clamping said tubular element between said sleeve and the said collar for forming said seal, whereby a pressure differential can be created across the back folded end of the tubular element to cause said end to travel along the tube-like opening as the tube unfolds.

6. An apparatus as described in claim 5 wherein said tubular nozzle is tapered and, except at said collar, is of a cross-sectional size to space it from the inside wall of said sleeve.

7. An apparatus as described in claim 6 wherein said attachment member engages said collar and clamps said sleeve thereto.

8. An apparatus as described in claim 7 wherein said attachment member is a ring threadably engaged to said collar.

9. The apparatus as described in claim 5 wherein the exterior surface of the outer end of said sleeve is tapered to provide a guiding surface to facilitate the insertion of said nozzle and sleeve into the end of said tube-like member.

* * * * *

UNITED STATES PATENT AND TRADEMARK OFFICE
CERTIFICATE OF CORRECTION

PATENT NO. : 4,077,610
DATED : March 7, 1978
INVENTOR(S) : Senichi Masuda

It is certified that error appears in the above-identified patent and that said Letters Patent are hereby corrected as shown below:

Column 1, lines 8 and 9:

"CROSS REFERENCE TO RELATED APPLICATION" should appear before --This is a continuation of application Ser. No. 646,950 filed Jan. 6, 1976, now abandoned.--

Column 1, line 38:

Delete "proof of"

Cancel "prominate" and substitute --proximate--

Column 2, line 19:

Cancel "collapases" and substitute --collapses--

Signed and Sealed this

Tenth Day of July 1979

[SEAL]

Attest:

Attesting Officer

LUTRELLE F. PARKER
Acting Commissioner of Patents and Trademarks